United States Patent [19]

Le Blanc et al.

[11] Patent Number: 4,496,763
[45] Date of Patent: Jan. 29, 1985

[54] PROCESS FOR THE PREPARATION OF ALKYL-SUBSTITUTED ANILINES

[75] Inventors: Helmut Le Blanc, Burscheid; Karlfried Wedemeyer, Cologne, both of Fed. Rep. of Germany

[73] Assignee: Bayer Aktiengesellschaft, Leverkusen, Fed. Rep. of Germany

[21] Appl. No.: 386,563

[22] Filed: Jun. 9, 1982

[30] Foreign Application Priority Data

Jun. 27, 1981 [DE] Fed. Rep. of Germany ....... 3125295
Dec. 2, 1981 [DE] Fed. Rep. of Germany ....... 3147734

[51] Int. Cl.$^3$ .............................................. C07C 85/06
[52] U.S. Cl. .................................................. 564/402
[58] Field of Search ........................................ 564/402

[56] References Cited

U.S. PATENT DOCUMENTS

| | | | |
|---|---|---|---|
| 1,935,209 | 11/1933 | Herold et al. | 564/402 |
| 2,013,873 | 9/1935 | Vogt | 564/402 |
| 3,272,865 | 9/1966 | Barker . | |
| 3,860,650 | 1/1975 | Becker et al. | 564/402 |
| 3,931,298 | 1/1976 | Wollensak | 564/402 |
| 3,952,056 | 4/1976 | Vogel et al. | 564/214 |
| 4,019,894 | 4/1977 | Vogel et al. | 71/118 |
| 4,380,669 | 4/1983 | Chang et al. | 564/402 |

FOREIGN PATENT DOCUMENTS

| | | | |
|---|---|---|---|
| 456604 | 5/1949 | Canada | 564/402 |
| 42568 | 12/1981 | European Pat. Off. . | |
| 2003842 | 7/1970 | Fed. Rep. of Germany . | |
| 2026053 | 12/1970 | Fed. Rep. of Germany . | |
| 2516316 | 10/1976 | Fed. Rep. of Germany . | |
| 3013401 | 10/1981 | Fed. Rep. of Germany . | |

OTHER PUBLICATIONS

Chemical Abstracts, vol. 81, 1974, pp. 387, *American Chemical Society,* Columbus, Ohio, "Aromatic amines," Mitsui Petrochemical Industries, Ltd. (10–04–1974) The entire document.
Chemical Abstracts, vol. 81, 1974, pp. 387, American Chemical Society, Columbus, Ohio, & JP A 74 14 737 (Mitsui Petrochemical Industries, Ltd.) (10–04–1974) The entire document.

*Primary Examiner*—William R. Dixon, Jr.
*Assistant Examiner*—Margaret B. Medley
*Attorney, Agent, or Firm*—Sprung Horn Kramer & Woods

[57] ABSTRACT

The invention relates to a process for the preparation of alkyl-substituted anilines by the reaction of alkyl-substituted phenols in the vapor phase with ammonia in the presence of an aluminium oxide catalyst, the starting materials being passed through the reactor at a particular flow rate.

Alkyl-substituted anilines are intermediate products for the preparation of herbicides.

18 Claims, No Drawings

PROCESS FOR THE PREPARATION OF ALKYL-SUBSTITUTED ANILINES

BACKGROUND OF THE INVENTION

The invention relates to a process for the preparation of alkyl-substituted anilines by the reaction of alkyl-substituted phenols in the vapor phase with ammonia in the presence of an aluminum oxide catalyst.

It is known that phenols can be reacted in the vapor phase with ammonia, under pressure and over catalysts containing aluminum oxide, to give the corresponding anilines (U.S. Pat. No. 1,935,209; U.S. Pat. No. 2,013,873; U.S. Pat. No. 3,272,865, German Auslegeschrift No. 2,026,053 and German Offenlegungsschrift No. 2,003,842). Although a large number of phenols are listed in the stated publications as being suitable starting compounds for the reaction, only a few phenols, in particular phenol itself, m- and p-cresol and 3,5-xylenol, are employed in the examples given therein (U.S. Pat. Nos. 3,272,865; 1,935,209 and 2,013,873).

According to German Offenlegungsschrift No. 2,516,316, difficulties arise in amination reactions with substituted phenols. Thus, for example, it is mentioned that up to 10% of by-products are formed when m-cresol is used. To avoid these disadvantages, German Offenlegungsschrift No. 2,516,316 recommends the addition of toluene. According to the examples of German Offenlegungsschrift No. 2,516,316, 2 parts by volume of toluene are added per part by volume of phenol, and the toluene must subsequently be separated off from the product mixture by distillation, condensed, and recycled. In addition to the increased outlay of apparatus required for this purpose, the use of the readily inflammable toluene at the high reaction temperatures is also unacceptable for reasons of safety.

According to Japanese Patent Application No. 49-29 176 (1974), m-toluidine is formed with a selectivity of only 81% in the reaction of m-cresol with ammonia in the gas phase.

SUMMARY OF THE INVENTION

A process for the preparation of alkyl-substituted anilines by the reaction of alkyl-substituted phenols in the vapor phase with ammonia in the presence of an aluminium oxide catalyst has now been found, which is characterized in that the starting materials in the vapor state are passed through the reactor at a flow rate of at least 20 cm/hour (relative to liquid volumes).

Alkyl-substituted phenols of the general formula

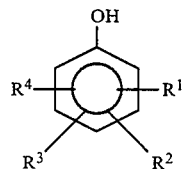

wherein
R[1] to R[4] are identical or different and represent hydrogen or straight-chain or branched or cyclic alkyl radicals, and wherein at least one radical denotes straight-chain or branched or cyclic alkyl, can be employed as the starting material.

Straight-chain or branched or cyclic alkyl radicals which may be mentioned are those having 1 to 7 carbon atoms, preferably 1 to 3 carbon atoms, for example the methyl, ethyl, n-propyl, iso-propyl, n-butyl, iso-butyl, tert.-butyl, hexyl, cyclohexyl and methylcyclohexyl radical, preferably the methyl radical.

For example, the isomeric cresols and xylenols, preferably m-cresol and 2,6-xylenol, are employed as starting materials. The upper limit of the flow rate is given only by technical factors, for example by excessive pressure loss or excessive abraisive wear of the catalyst. Usually, the flow rate is adjusted only as high as to complete the conversion of the starting material to the wanted alkyl-substituted anilines as much as possible and no unconverted phenol has to be separated off. The starting materials, consisting of NH$_3$ and alkyl-substituted phenol, are passed through the reactor, via a vaporizer, preferably at a flow rate of from 20 to 3,200 cm)hour, particularly preferably at a flow rate of from 160 to 1,600 cm)hour. In this context, the flow rate v is defined as follows:

$$v = \frac{\text{Throughput of the liquid volumes of NH}_3 \text{ and alkyl-substituted phenol}}{\text{Base area of the reactor} \cdot \text{time}} \left[\frac{cm^3}{cm^2 \cdot hour}\right] = \left[\frac{cm}{hour}\right]$$

The volumes given for NH$_3$ and the alkyl-substituted phenol relate to liquid NH$_3$ (d=0.58 at 40° C.) and liquid molten alkylphenol (d about 1.0 if liquid/molten at 60° C.).

To increase the flow rate the starting materials can be mixed with inert gases, such as nitrogen and/or hydrogen and/or noble gases, such as helium, neon, argon, krypton and/or xenon, and/or vapors, such as water vapors, and/or vapors of organic compounds which are inert under the reaction conditions, such as benzene, toluene, diphenyl and/or diphenyl ether. In general 0.1 to 50 mol %, preferably 2 to 30 mol %, relative to the ammonia/phenol mixture, of inert gases and/or vapors is added to the starting materials.

The process according to the invention is customarily carried out using a molar ratio of ammonia to phenol of at least about 2:1, and a minimum pressure of about 15 bar. Both the ammonia/alkylphenol molar ratio and the pressure have upper limits determined only by technical and economic factors. The process according to the invention is carried out using a molar ratio of ammonia to the alkylphenol employed of preferably from 2:1 to 140:1, particularly preferably from 3:1 to 75:1, and under pressures of from 15 to 250, particularly preferably from 70 to 220, bar.

The process according to the invention is carried out in general at temperatures of about 360° to 460° C., preferably at 380° to 440° C., particularly preferably at 400° to 430° C.

Aluminum oxide catalysts have proved suitable as the catalysts. Aluminum oxide catalysts which contain at least 95% by weight of aluminum oxide, less than 0.5% of alkali metal (given as the alkali metal oxide) and less than 0.5% iron (given as iron oxide) are preferably employed in the process according to the invention. A very pure aluminum oxide catalyst which contains at most 0.2% by weight of alkali metal (given as the alkali metal oxide) and at most 0.3% by weight of iron metal (given as iron oxide) is particularly preferably employed.

The aluminum oxide catalysts to be employed can be used in the form of pellets or beads, and pellets having a diameter of from about 0.5 mm to about 10 mm are preferably employed.

DETAILED DESCRIPTION OF THE INVENTION

The process according to the invention can be carried out, for example, as follows:

Liquid alkylphenol and liquid ammonia are fed to a vaporizer at a flow rate greater than 20 cm/hour, are vaporized together therein, and are then passed, under pressure and at relatively high temperatures, through a tubular reactor charged with the aluminum oxide catalyst. The pressure of the reaction mixture leaving the reactor is released, and the mixture is condensed. The condensate is then fractionally distilled in a manner which is in itself known. To recycle the unreacted portion of ammonia, the ammonia can be distilled off from the product mixture at approx. 50 bar, and circulated.

According to another variant of the process according to the invention, liquid ammonia and liquid alkylphenol can also be vaporized separately and mixed only before entry into the reactor.

It is also possible for the phenol to be heated up and vaporized by superheated $NH_3$.

Additives such as water and/or inert organic solvents can be vaporized together with the $NH_3$/phenol mixture or with one of the two reactants. The water and/or the inert organic solvent can also be vaporized separately and metered into the reactants only before entry into the reactor.

The process according to the invention can be carried out discontinuously as well as continuously.

With the aid of the process according to the invention, alkyl-substituted anilines can be obtained in high selectivity with good space-time yields, as shown in the experimental examples.

With the aid of the process according to the invention not only the yield of the wanted substituted aniline is increased but, what is of even greater importance, the amount of unwanted by-products which can only difficultly removed, is sharply decreased. Thus, with the aid of the inventive process highly pure alkyl-substituted anilines can be produced starting from the respective phenols.

Surprisingly, the process according to the invention is particularly suitable for the preparation of 2,6-xylidine from 2,6-xylenol, which is obtained virtually free from the interfacing isomeric 2,4- and 2,5-xylidines. The isolation of the 2,6-xylidine in over 99% purity without difficulties is therefore assured.

This is the more surprising since 2,6-xylidine has hitherto been prepared by complicated processes according to German Auslegeschrift No. 1,933,636 and German Auslegeschrift No. 2,208,827, and it has not been possible under the known amination conditions to prepare 2,6-xylidine in good yields and free from interfering isomers. Thus, the reaction of 2,6-xylenol with ammonia in the gas phase under the amination conditions described in German Auslegeschrift No. 2,026,053 gives only an unsatisfactory yield of 2,6-xylidine. In addition, the reaction proceeds with a poor selectivity and with the formation of substantial proportions of isomeric 2,4- and 2,5-xylidines, which cause great difficulties in the working-up since the 2,4-dimethylaniline, in particular, cannot be separated off or can be separated off only by a very complicated distillation.

2,6-Xylidine is an intermediate product for the preparation of herbicides (see German Offenlegungsschrift No. 2,648,008, German Offenlegungsschrift No. 2,305,495, U.S. Pat. Nos. 3,952,056 and 4,019,894).

The process according to the invention is illustrated by the examples which follow:

EXAMPLE 1

A reactor which has a length of 76 cm and a diameter of 1 cm and which is charged with 60 ml of aluminum oxide catalyst (particle size: 0.5 to 1.0 mm) is heated to 400° C. in a salt bath.

A mixture of 39.3 ml of liquid ammonia and 2.7 ml of 2,6-xylenol (molar ratio 60:1) is vaporized, per hour, in a pre-vaporizer, and the gas mixture, brought to the reaction temperature and under a pressure of 190 bar, is passed through the reactor. The starting materials are passed through the reactor at a flow rate of 53.5 cm/hour (relative to liquid volumes). The xylidine mixture, the pressure of which has been released, is condensed and analyzed by gas chromatography. The product has the following composition:

0.76% of aniline,
1.87% of o-toluidine,
1.41% of p-toluidine,
93.2% of 2,6-xylidine,
0.08% of 2,4-xylidine,
0.13% of 2,5-xylidine,
0.23% of 2,6-xylenol and
1.43% of 2,4,6-mesidine.

EXAMPLE 2

(Comparative Example)

The procedure of Example 1 is repeated, with the following change: a mixture of 13.6 ml of ammonia and 0.9 ml of 2,6-xylenol (molar ratio 60:1) is vaporized, per hour, and is passed through the reactor at a flow rate of 18.5 cm/hour (relative to liquid volumes). The product mixture has the following composition:

0.74% of aniline,
2.7% of o-toluidine,
1.3% of p-toluidine,
92.0% of 2,6-xylidine,
0.14% of 2,4-xylidine,
0.12% of 2,5-xylidine,
0.18% of 2,6-xylenol and
2.4% of 2,4,6-mesidine.

EXAMPLE 3

(Comparative Example)

The procedure of Example 1 is repeated, with the following change: a mixture of 4.2 ml of ammonia and 0.3 ml of 2,6-xylenol (molar ratio 60:1) is vaporised, per hour, and is passed through the reactor at a flow rate of 5.7 cm/hour (relative to liquid volumes).

The product mixture has the following composition:
0.5% of aniline,
3.2% of o-toluidine,
1.06% of p-toluidine,
91.4% of 2,6-xylidine,
0.22% of 2,4-xylidine,
0.13% of 2,5-xylidine,
0.18% of 2,6-xylenol and
3.0% of 2,4,6-mesidine.

EXAMPLE 4

The procedure of Example 1 is repeated, with the following change: a mixture of 57.6 ml of ammonia and 2.0 ml of 2,6-xylenol (molar ratio 120:1) is vaporized, per hour, and is passed through the reactor at a flow rate of 75.9 cm/hour (relative to liquid volumes). The product has the following composition:
0.53% of aniline,
1.56% of o-toluidine,
1.17% of p-toluidine,
92.8% of 2,6-xylidine,
0.08% of 2,4-xylidine,
0.12% of 2,5-xylidine,
2.0% of 2,6-xylenol and
1.31% of 2,4,6-mesidine.

EXAMPLE 5

(Comparative Example)

The procedure of Example 1 is repeated, with the following change: a mixture of 3.0 ml of ammonia and 0.1 ml of 2,6-xylenol (molar ratio 120:1) is vaporized, per hour, and is passed through the reactor at a flow rate of 3.9 cm/hour (relative to liquid volumes).

The product mixture has the following composition:
0.69% of aniline,
4.0% of o-toluidine,
1.18% of p-toluidine,
90.0% of 2,6-xylidine,
0.29% of 2,4-xylidine,
0.11% of 2,5-xylidine,
0.08% of 2,6-xylenol and
2.8% of 2,4,6-mesidine.

EXAMPLE 6

The procedure of Example 1 is repeated, with the following change: a mixture of 22.1 ml of ammonia and 3.1 ml of 2,6-xylenol (molar ratio 30:1) is vaporized, per hour, and is passed through the reactor at a flow rate of 32.1 cm/hour (relative to liquid volumes).

The product has the following composition:
0.8% of aniline,
3.0% of o-toluidine,
1.31% of p-toluidine,
92.0% of 2,6-xylidine,
0.22% of 2,4-xylidine,
0.12% of 2,5-xylidine,
0.33% of 2,6-xylenol and
1.75% of 2,4,6-mesidine.

EXAMPLE 7

(Comparative Example)

The procedure of Example 1 is repeated, with the following change: a mixture of 8.9 ml of ammonia and 1.2 ml of 2,6-xylenol (molar ratio 30:1) is vaporized, per hour, and is passed through the reactor at a flow rate of 12.9 cm/hour (relative to liquid volumes).

The product mixture has the following composition:
0.82% of aniline,
5.9% of o-toluidine,
1.0% of p-toluidine,
87.84% of 2,6-xylidine,
0.57% of 2,4-xylidine,
0.14% of 2,5-xylidine,
0.47% of 2,6-xylenol and
2.76% of 2,4,6-mesidine.

EXAMPLE 8

(Addition of water)

A reactor which has a length of 34 cm and a diameter of 1 cm and which is charged with 27 ml of aluminum oxide catalyst (particle size 0.5 to 1.0 mm) is heated to 400° C. in a salt bath.

A mixture of 15.3 ml of liquid ammonia, 1.1 ml of 2,6-xylenol and 1.0 ml of water is vaporized, per hour, in a pre-vaporizer, and the gas mixture at 400° C. and under a pressure of 190 bar is passed through the reactor at flow rate of 22.2 cm/hour (relative to liquid volumes).

The xylidine mixture, the pressure of which has been released, is condensed and analyzed by gas chromatography. The product has the following composition:
0.68% of aniline,
2.6% of o-toluidine,
0.7% of p-toluidine.
91.8% of 2,6-xylidine,
0.10% of 2,4-xylidine,
0.02% of 2,5-xylidine,
1.0% of 2,6-xylenol and
2.4% of 2,4,6-mesidine.

EXAMPLE 9

A reactor which has a length of 34 cm and a diameter of 1.0 cm and which is charged with 27 ml of $Al_2O_3$ catalyst (particle size 0.5 to 1.0 mm) is heated to 430° C. in a salt bath.

A mixture of 41.0 ml of liquid $NH_3$ and 10.1 ml of o-cresol (molar ratio 15:1) is vaporized, per hour, in a pre-vaporizer, and the gas mixture, brought to the reaction temperature and under a pressure of 190 bar, is passed through the reactor. The starting materials are passed through the reactor at a flow rate of 65.0 cm/hour (relative to liquid volumes). The toluidine mixture, the pressure of which has been released, is condensed and analyzed by gas chromatography.

The product has the following composition:
1.3% of aniline,
96.7% of o-toluidine,
0.26% of m-toluidine,
0.61% of 2,4-xylidine and
0.59% of o-cresol.

EXAMPLE 10

(Comparative Example)

The procedure of Example 9 is repeated, with the following change: a mixture of 4.7 ml of $NH_3$ and 1.2 ml of o-cresol (molar ratio 15:1) is vaporized per hour, and is passed through the reactor at a flow rate of 7.5 cm/hour (relative to liquid volumes).

The product mixture has the following composition:
3.0% of aniline,
92.68% of o-toluidine,
0.12% of p-toluidine,
1.23% of m-toluidine,
1.76% of 2,4-xylidine,
0.25% of 2,5-xylidine and
0.62% of o-cresol.

EXAMPLE 11

The procedure of Example 9 is repeated, with the following change: a mixture of 34 ml of $NH_3$ and 8.4 ml of p-cresol (molar ratio 15:1) is vaporized, per hour, and is passed through the reactor at a flow rate of 54.0 cm/hour (relative to liquid volumes).

The product mixture has the following composition:
0.31% of aniline,
0.12% of o-toluidine,
94.6% of p-toluidine,
1.62% of m-toluidine,
0.35% of 2,4-xylidine,
0.42% of p-cresol and
1.72% of 4,4'-dimethyl-diphenylamine.

EXAMPLE 12

(Comparative Example)

The procedure of Example 9 is repeated, with the following change: a mixture of 7.9 ml of NH₃ and 2.0 ml of p-cresol (molar ratio 15:1) is vaporized, per hour, and is passed through the reactor at a flow rate of 12.7 cm/hour (relative to liquid volumes).

The product mixture has the following composition:
6.7% of aniline,
0.58% of o-toluidine,
79.0% of p-toluidine,
1.61% of m-toluidine,
4.8% of 2,4-xylidine,
0.49% of p-cresol and
2.7% of 4,4'-dimethyl-diphenylamine.

EXAMPLE 13

The procedure of Example 9 is repeated, with the following change: a mixture of 39.0 ml of NH₃ and 9.6 ml of m-cresol (molar ratio 15:1) is vaporized, per hour, and is passed through the reactor at a flow rate of 61.8 cm/hour (relative to liquid volumes).

The product mixture has the following compossition:
98.5% of m-toluidine,
0.14% of m-cresol and
1.16% of 3,3'-dimethyl-diphenylamine.

EXAMPLE 14

(Comparative Example)

The procedure of Example 9 is repeated, with the following change: a mixture of 3.5 ml of NH₃ and 0.9 ml of m-cresol (molar ratio 15:1) is vaporized, per hour, and is passed through the reactor at a flow rate of 5.6 cm/hour (relative to liquid volumes).

The product mixture has the following composition:
90.0% of m-toluidine,
0.49% of m-cresol and
9.0% of 3,3'-dimethyl-diphenylamine.

EXAMPLE 15

The procedure of Example 1 is repeated, with the following change: a mixture of 13.1 ml of NH₃ and 4.1 ml of o-isopropylphenol (molar ratio 15:1) is vaporized, per hour, and is passed through the reactor at a flow rate of 21.8 cm/hour (relative to liquid volumes).

The product mixture has the following composition:
8.4% of aniline,
74.0% of o-isopropyl-aniline,
11.8% of o-n-propylaniline
0.25% of m-isopropyl-aniline,
0.35% of p-isopropyl-aniline and
0.56% of o-isopropyl-phenol.

EXAMPLE 16

(Comparative Example)

The procedure of Example 1 is repeated, with the following change: a mixture of 8.5 ml of NH₃ and 2.6 ml of o-isopropylphenol (molar ratio 15:1) is vaporized, per hour, and is passed through the reactor at a flow rate of 14.2 cm/hour (relative to liquid volumes).

The product mixture has the following composition:
10.7% of aniline,
69.3% of o-isopropyl-aniline,
13.3% of o-n-propylaniline
0.28% of m-isopropyl-aniline,
0.47% of p-isopropyl-aniline and
0.63% of o-isopropyl-phenol.

What is claimed is:

1. In a process for the preparation of an alkyl-substituted aniline by contacting an alkyl substituted phenol in the vapor phase with ammonia in the presence of an aluminum oxide catalyst, the improvement wherein the process is carried out by passing said alkyl-substituted phenol and ammonia in the vapor phase through a reactor containing said aluminum oxide catalyst at a flow rate of at least 20 cm/hour, relative to liquid volumes using a molar ratio of ammonia to phenol of at least about 2:1, and a minimum pressure of 15 bars and at a temperature of about 360° to 460° C.

2. A process according to claim 1, wherein said flow rate is from 20 to 3,200 cm/hour.

3. A process according to claim 1, wherein said flow rate is from 160 to 1600 cm/hour.

4. A process according to claim 1, wherein an inert gas or vapor is mixed with said mixture of ammonia and alkyl substituted phenol to increase the flow rate.

5. A process according to claim 4, wherein said inert gas or vapor is selected from the group consisting of nitrogen, hydrogen, a noble gas, water vapor, a vapor of an inert organic compound andd a mixture thereof.

6. A process according to claim 1, wherein 0.1 to 50 mol % relative to the ammonia/alkyl phenol mixture of inert gas or vapor is added to the mixture of ammonia and alkyl phenol.

7. A process according to claim 6, wherein 2 to 30 mol %, based upon the combined amount of alkyl phenol and ammonia, of inert gas or vapor is added to the mixture of ammonia and alkyl phenol.

8. A process according to claim 1, wherein said alkyl phenol is one of the formula

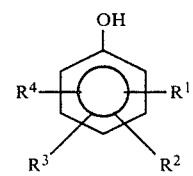

wherein
$R^1$ to $R^4$ are identical or different and represent hydrogen or straight-chain or branched or cyclic alkyl radicals, wherein at least one radical denotes a straight-chain or branched or cyclic alkyl having 1 to 7 carbon atoms.

9. A process according to claim 1, wherein said alkyl phenol is 2,6-xylenol.

10. A process according to claim 1, wherein said alkyl phenol is o, m or p cresol.

11. A process according to claim 1, wherein said alkylphenol is o-isopropyl-phenol.

12. A process according to claim 8, wherein said straight-chain or branched or cyclic alkyl radicals have 1 to 7 carbon atoms.

13. A process according to claim 1, wherein said ammonia and said alkylphenol are in a molar ratio of ammonia to alkylphenol of 2:1 to 140:1.

14. A process according to claim 13, wherein said ammonia and said alkylphenol are in a molar ratio of ammonia to alkylphenol of 3:1 to 75:1.

15. A process according to claim 13, wherein the process is conducted at a pressure of 15 to 250 bars.

16. A process according to claim 15, wherein the process is conducted at a pressure of 70 to 220 bars.

17. A process according to claim 1, wherein the process is conducted at a temperature of 380° C. to 440° C.

18. A process according to claim 17, wherein the process is conducted at a temperature of 400° C. to 430° C.

* * * * *